US00PP21398P3

(12) United States Plant Patent
Bourne

(10) Patent No.: US PP21,398 P3
(45) Date of Patent: Oct. 19, 2010

(54) *DIANTHUS* PLANT NAMED 'WP08 IAN04'

(50) Latin Name: *Dianthus×hybrida*
Varietal Denomination: WP08 IAN04

(76) Inventor: Carolyn Grace Bourne, Houndspool Ashcombe Road, Dawlish, Devon (GB) EX7 0QP ( * ) Notice: Subject to any disclaimer, the term of this patent is extended or adjusted under 35 U.S.C. 154(b) by 0 days.

(21) Appl. No.: 12/456,880

(22) Filed: Jun. 23, 2009

(65) Prior Publication Data

US 2009/0328262 P1 Dec. 31, 2009

(51) Int. Cl.
*A01H 5/00* (2006.01)

(52) U.S. Cl. ..... Plt./283

(58) Field of Classification Search ..... Plt./283
See application file for complete search history.

*Primary Examiner*—Annette H Para

(57) ABSTRACT

A new cultivar of *Dianthus* plant named 'WP08 IAN04' that is characterized by pronounced compact habit, grey-green foliage, and flowers that are double and whose petal grounds are bright cherry red with a pale pink margin, and which bloom from April through October. In combination these traits set 'WP08 IAN04' apart from all other existing varieties of *Dianthus* known to the inventor.

2 Drawing Sheets

Genus: *Dianthus.*
Species: ×*hybrida.*
Denomination: 'WP08 IAN04'.

BACKGROUND OF THE INVENTION

This application claims the benefit of priority under 35 U.S.C. 119(f) of the application for a grant of European Community Plant Breeders Rights which was filed for the instant plant variety on Jun. 30, 2008, Application Number 2008/1511.

The present invention relates to a new and distinct cultivar of hardy garden pink or carnation which is grown for use as a flowering plant for pots and containers and for planting in the garden or landscape. The new cultivar is known botanically as *Dianthus×hybrida* and will be referred to hereinafter by the cultivar name 'WP08 IAN04'.

'WP08 IAN04' is a complex hybrid plant that is the product of a breeding program started by the inventor in 1985. The breeding program is conducted in a cultivated area of Houndspool, Dawlish, Devon, United Kingdom. The inventor selected 'WP08 IAN04' in 2004 for its flowers that are double and whose petal grounds are bright cherry red with a pale pink margin, and which bloom from April through October.

'WP08 IAN04' resulted from the controlled pollination between two unreleased and unpatented varieties, namely *Dianthus* code number FLA 02.28 as female parent plant and *Dianthus* code number 99.17 as male parent plant.

'WP08 IAN04' is distinguishable from the female parent as follows: The female parent is smaller in height with light pink flowers.

'WP08 IAN04' is distinguishable from the male parent as follows: The male parent is taller in height and has large single flower whose color is carmine with white border. In addition, the buds of 'WP08 IAN04' exhibit a chocolate brown coloration.

The variety of *Dianthus* which is considered by the inventor to most closely resemble 'WP08 IAN04' is the inventor's variety *Dianthus* 'Coral Reef' (U.S. Plant Pat. No. 19,660).

'WP08 IAN04' is distinguishable from this variety as follows: 'Coral Reef' bears lighter salmon-pink flowers with a pale pink edge.

Asexual reproduction of the new cultivar was first accomplished by the inventor in 2000 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP08 IAN04'. These traits in combination distinguish this cultivar from all other commercial varieties known to the inventor. 'WP08 IAN04' has not been tested under all possible conditions and phenotypic differences may be observed with variations in environmental, climatic and cultural conditions, however, without any variance in genotype.

1. *Dianthus* 'WP08 IAN04' exhibits a compact habit.
2. *Dianthus* 'WP08 IAN04' blooms profusely from April until October.
3. *Dianthus* 'WP08 IAN04' exhibits double flowers that are bright cherry red with a pale pink edge.
4. *Dianthus* 'WP08 IAN04' exhibits grey-green foliage.
5. After nine months of growth, the height of the foliage mound of *Dianthus* 'WP08 IAN04' is 30 cm to 35 cm; the width is 14 cm to 16 cm.
6. *Dianthus* 'WP08 IAN04' is perennial and is hardy to −15° C.

BRIEF DESCRIPTION OF THE DRAWINGS

The accompanying color drawings illustrate the overall appearance of the new *Dianthus* variety 'WP08 IAN04' showing colors as true as it is reasonably possible to obtain in colored reproductions of this type. Colors in the drawings may differ from the color values cited in the detailed botanical description, which accurately describe the actual colors of the new variety 'WP08 IAN04'.

The drawing labeled as FIG. 1 depicts an entire flowering plant.

Figure 1:
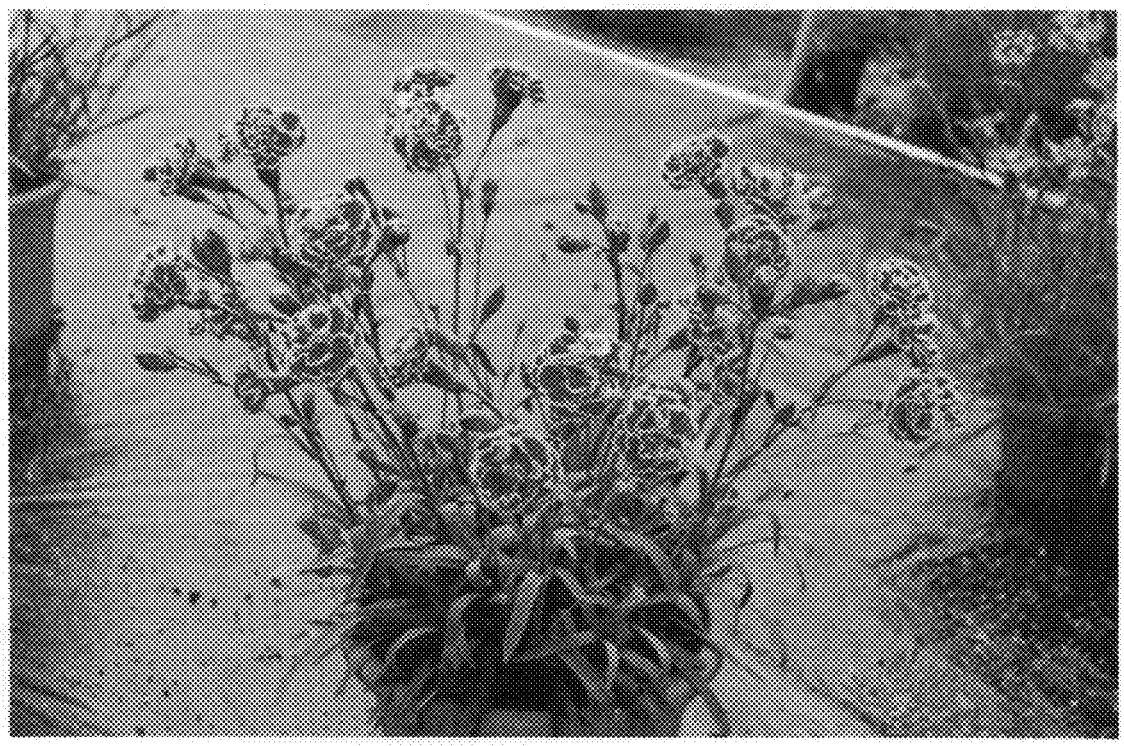
Figure 2:
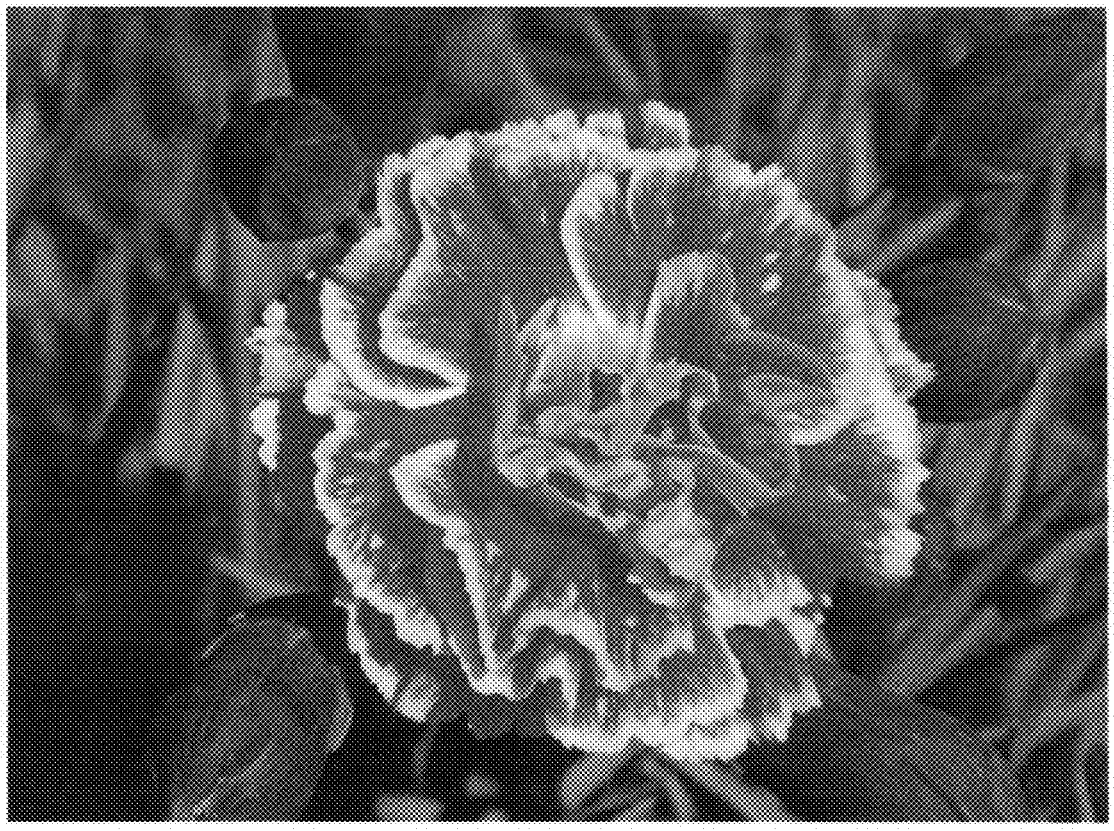

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP08 IAN04'. Data was collected in spring from 1.5-liter container plants in spring, and grown indoors in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family.*—Caryophyllaceae.
- *Genus.*—*Dianthus.*
- *Species.*—×*allwoodii.*
- *Denomination.*—'WP08 IAN04'.

Parentage: A complex *Dianthus* hybrid whose immediate parents are unreleased hybrids from the inventor's breeding program, identified as follows:
- *Male parent.*—Selection 99.17.
- *Female parent.*—Selection FLA 02.28.

Plant type: Flowering perennial.

Use of plant: As a flowering plant in containers, window boxes, planters, pots and the garden.

Bloom period: April-October.

Plant habit: A compact mound with many branches and stems upright.

Height of plant: 30 to 35 cm after 9 months.

Width of plant: 14 to 16 cm after 9 months.

Hardiness: Plants have survived in temperatures as low as minus 15 Centigrade.

Root system: Many fibrous roots.

Propagation method: Vegetative stem cuttings.

Cultural requirements: Grow in full sun, in well drained and moderately fertile soil, keep well fertilized and watered.

Diseases and pests: No particular susceptibility or resistance to *Dianthus* diseases and pests are known to the inventor Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: Mist propagation unit is recommended for satisfactory rooting of cuttings.

Crop time: 3 months if starting in the Spring and 6 months if starting in the Fall.

Plant stem:
- *Shape.*—Cylindrical.
- *Height.*—10 to 15 cm.
- *Diameter.*—5 mm.
- *Surface.*—Glabrous and glaucous.
- *Color.*—144C.
- *Branching.*—Numerous shoots from the axils of the lower leaves.
- *Internode length* (*between nodes*).—6 mm.

Leaf:
- *Type.*—Evergreen.
- *Shape.*—Linear, slightly curled at the base of the plant and straight towards the apex.
- *Division.*—Simple.
- *Apex.*—Acute.
- *Base.*—Decurrent.
- *Venation.*—Not prominent.
- *Margins.*—Entire.
- *Arrangement.*—Opposite and spiraling on stem.
- *Attachment.*—Sheathing.
- *Surface adaxial.*—Glaucous.
- *Surface abaxial.*—Glaucous.
- *Fragrance.*—Absent.
- *Dimensions.*—Length: 85 to 105 mm. Width: 5 mm.
- *Color.*—Adaxial surface: 189A-189B. Abaxial surface: 189A-189B.

Inflorescence:
- *Flower stem.*—Length: 25 to 30 cm. Width: 4 mm. Stem strength: Stiff, erect. Color: N189C-188B.
- *Type.*—Cymose.
- *Form.*—Salviform, symmetrical.
- *Development.*—Singly, in sequence from the uppermost bud.

Buds:
- *Color.*—183D.
- *Dimensions.*—15 mm. in length and 9 mm. in width.
- *Bud shape.*—Cylindrical.

Flowers:
- *Number.*—4 to 6 per stem.
- *Dimensions.*—Length (including calyx): 38 mm. Diameter: 40 mm.
- *Flower shape.*—Circular.
- *Flower profile.*—Concave to convex.
- *Lastingness.*—10 days at 20° C., on or off the plant.
- *Fragrance.*—Medium.
- *Flowering period.*—April to October (unforced).

Corolla:
- *Shape* (*upper part of corolla*).—Convex.
- *Shape* (*lower part of corolla*).—Concave.
- *Petal arrangement.*—Persistent, double, overlapping.
- *Petal margin.*—Crenate to dentate.
- *Indentation.*—Varies from 0 mm to 2 mm.
- *Petal texture.*—Soft.
- *Petal number.*—10 to 15 (including approximately 5 petaloids).
- *Petal dimension.*—Length: 38 to 40 mm. Width: 21 to 24 mm.
- *Color pattern.*—Petal blade is red with a pale pink margin which bleeds into the main color.
- *Color of upper surface.*—Ground color of blade: N57A-N57B. Color of margin (extends 3 mm inward before bleeding into ground color): 62C. Color of middle of strap (basal attachment): 145C-145B. Color of base of strap: 145C-145D.
- *Color of lower surface.*—Ground color of blade: 68B-68D. Color of margin (extends 3 mm inward before bleeding into ground color): 62C. Color of middle of strap: 145C-145B. Color of base of strap: 145C-145D.

Petal shape: Obdeltoid.

*Petal surface.*—Glabrous, undulating.

Calyx:

*Shape.*—Cylindrical.

*Longitudinal profile.*—Flat to slightly convex.

*Dimensions.*—Length: 24 mm. Diameter: 10 mm.

*Sepals.*—Fused.

*Sepals number.*—5.

*Sepals color.*—N138A-N138C.

*Anthocyanin.*—Present, whole calyx.

*Splitting.*—No.

Epicalyx:

*Bracts number.*—2 (arranged as a pair).

*Shape of outer lobe.*—Acuminate.

*Dimensions.*—Width: 7 to 9 mm. Length: 10 to 12 mm.

*Color.*—139A at apex, 143B elsewhere.

*Anthocyanin.*—Present.

*Bracteole number.*—2.

*Dimensions.*—Width: 12 mm. Length: 10 mm.

*Color.*—139A at the apex, 143B elsewhere.

*Anthocyanin.*—Present.

Reproductive organs:

*Stamens.*—Number: Usually 5, some deformed or petaloid. Color of filaments: White with a purple flush close to the anther. Dimensions: Length: 28 mm. Diameter: 0.5 to 1 mm.

*Anthers.*—Number: Usually 5, mostly malformed. Color: 70D to N74C. Dimensions: Length: 5 mm. Diameter: 1 to 2 mm. Attachment: Basifixed.

*Pollen.*—Present on well-formed anthers. Slight quantity.

*Pollen color.*—157A.

*Style.*—Number: 2 Color: White.

*Dimensions.*—Length: 19 mm. Width: 0.5 mm.

*Stigma.*—Color: 70B. Length: 5 mm.

*Ovary.*—Position: Superior. Dimensions: Length: 7 mm. Diameter: 4 mm. Shape: Spindle. Color (upper surface): 145B. Color (lower surface): 145C.

*Seed.*—Seed has not been observed.

The invention claimed is:

1. A new and distinct cultivar of *Dianthus* plant named 'WP08 IAN04' as described and illustrated herein.

* * * * *